United States Patent [19]

Aziz

[11] Patent Number: 4,883,073
[45] Date of Patent: Nov. 28, 1989

[54] REMEDIAL DEVICE FOR TREATMENT OF CARPAL TUNNEL SYNDROME

[76] Inventor: Farooq Aziz, 3755 Warrensville Center Rd., Apt. #3, Shaker Heights, Ohio 44122

[21] Appl. No.: 375,527

[22] Filed: Jul. 3, 1989

[51] Int. Cl.⁴ .............................................. A61F 5/00
[52] U.S. Cl. .................. 128/878; 128/87 R; 128/77
[58] Field of Search .................. 128/877, 878, 879, 77, 128/87 R, 89 R

[56] References Cited

U.S. PATENT DOCUMENTS

| | | | |
|---|---|---|---|
| 3,829,090 | 8/1974 | Ensinger | 273/54 B |
| 4,183,098 | 1/1980 | Knowles, Jr. | 2/16 |
| 4,584,993 | 4/1986 | Nelson | 128/77 |
| 4,677,971 | 7/1987 | Lindemann | 128/87 R |
| 4,716,892 | 1/1988 | Brunswick | 128/77 |

Primary Examiner—Richard J. Johnson
Assistant Examiner—Lynda M. Cofsky
Attorney, Agent, or Firm—John F. McDevitt

[57] ABSTRACT

A therapeutic wrist support is provided allowing a person with carpal tunnel syndrome to manipulate the wrist without further aggravating this ailment. The device employs a flexible substrate which includes integral splint elements physically positioned to allow limited wrist movement in both vertical and horizontal directions with respect to the longitudinal axis of the wearer's forearm. Positioning of the splint elements is also made dependent upon whether the left or right wrist of the wearer is involved.

18 Claims, 1 Drawing Sheet ns with respect to the forearm longitudinal axis of a wearer.

Still another object of the invention is to provide improved treatment means with a wrist support construction better accommodating the particular wrist of the person affected by this ailment.

A still further object of the invention is to provide such wrist splinting device having all parts thereof integrally joined together so as to resist dislodgement while further enabling the wearer to easily apply and remove the device.

These and other objects of the present invention will become more apparent upon considering the following detailed description for the present invention.

REMEDIAL DEVICE FOR TREATMENT OF CARPAL TUNNEL SYNDROME

BACKGROUND OF THE INVENTION

This invention relates generally to the medical treatment of carpal tunnel syndrome and more particularly to an orthopedic support device intended to help relieve pressure when the wearer manipulates the injured wrist.

Carpal tunnel syndrome is a common and troublesome condition that interferes with the use of the hand. It is caused when too much pressure is put on the nerve that runs through the wrist region of a person. A variety of anatomical abnormalities may be responsible for a vise-like pressure occurring in the wrist region causing considerable pain to the affected person with the condition frequently worsening and resulting in permanent nerve damage. However, carpal tunnel syndrome can be treated effectively, especially if diagnosed early, with various types of treatment being already known. Medical treatment of this ailment includes splinting, medication, or both, and with surgery also being employed if the ailment persists. Progressive pain and numbness also frequently occurs if carpal tunnel syndrome is not treated effectively with the pain, numbness and tingling being experienced anywhere and anytime. The affected person often is awakened from sleep and the untreated condition can also cause a person's grip to weaken to the point of dropping things. The seriousness of ineffective treatment for this ailment is further evidenced by the fact that both wrists of a person are frequently involved to the point even light hand tasks cannot be tolerated.

Recovery from this ailment is also recognized to be a slow process often requiring the ailing person to wear a wrist support for many months while still refraining from even simple hand movements. Because simple hand tasks can further aggravate this condition, repetitive hand movements are often proscribed despite having the wrist supported in this manner and with maintaining of the supported wrist in a neutral unflexed condition being further recommended. The conventional splinting arrangement for this condition employs a single splint member extending longitudinally along the wearer's forearm into the hand region to primarily restrain vertical wrist movement. While such restraint upon vertical movement only has been regarded adequate to relieve pressure upon the nerve, it has also been recognized that such non-surgical treatment helps only temporarily in many cases. Moreover, the single splint member for such conventional splinting arrangement is commonly secured to the wearer's arm with temporary means such as elastic bandaging or a glove support for each application and removal by the wearer. Such a multipart wrist support construction becomes prone to further movement when worn thereby failing to provide the relief sought and possibly causing aggravated further injury upon movement. Accordingly, it still remains needed to provide improvement treatment for this ailment with a modified wrist supporting construction.

It is an object of the present invention, therefore, to provide improved means for the treatment of carpal tunnel syndrome with a remedial wrist support.

It is another object of the present invention to provide such remedial wrist support means permitting limited wrist mobility in both vertical and horizontal directions with respect to the forearm longitudinal axis of a wearer.

SUMMARY OF THE INVENTION

In general and in accordance with one aspect of the present invention, an improved remedial device for treatment of carpal tunnel syndrome is now provided which permits limited wrist mobility by the wearer in both vertical and horizontal directions comprising in combination: (a) flexible substrate sized to fit entirely around the wearer's forearm to form upper, lower and side portions when secured in place and which extends longitudinally at one end from a location below the wearer's elbow to an opposite palm end approaching the metacarpal joints of the wearer's hand, the palm end further terminating in an elastic cuff gripping the wearer's hand while also including a projection extending forwardly therefrom at the wearer's thumb before the device is secured in place but extending backwardly therefrom when secured in place, (b) a cushioning pad joined to the flexible substrate in the palm region, (c) a first longitudinally extending splint restraining excess vertical mobility of the wearer's wrist and joined to the flexible substrate in the upper portion, (d) a second longitudinally extending splint restraining excess horizontal mobility of the wearer's wrist and joined to the flexible substrate in a predetermined side portion, and (e) releasable fastening means joined to the flexible substrate enabling the side portions to be secured together while also enabling the hand projection to be secured to the top portion. The permitted wrist mobility with such device can be about the same in both vertical and horizontal directions with respect to the forearm longitudinal axis of a wearer and with such mobility in at least one of said directions not exceeding about ten degrees from the identified axis. To still further illustrate a typical device having such mobility restraint, the splint members in the device allow about a seven degree movement of the wrist in both lateral and vertical flexure thereby permitting a wearer to carry out most work tasks without unduly risking further aggravation of the ailment being treated. A predetermined location of the second splint member in the present device is also fixed by the left or right wrist involved with the condition. More particularly, such device for treatment of the condition in the left wrist has the second splint member physically located on the left side portion of the flexible support when secured in place. Correspondingly, such device locates the second splint member on the right side portion of the flexible support again when secured in place for treatment of the condition in the right wrist. The releasable fastening means being employed in the present device to secure easy attachment to the wearer's wrist as well as a like removal typically employ cooperating strips at side locations. Such strip elements employ hook and loop type fasteners on the strip which engage for ready connection, adjustment and release. In a preferred construction both splint members as well as the cushion pad in said device are permanently joined to the flexible substrate by conventional means. For example, a cloth substrate permits the splint members and cushioning pad to be sewn directly to the fabric along with a like joinder thereto of the elastic cuff located in the palm region of said cloth substrate. Pressure is relieved upon the ailing wrist with the present device by having the cushioning pad rest against the palm of a wearer.

In the above illustrated preferred embodiments, the flexible substrate overlaps the wearer's forearm with a plurality of releasable fastening strips being located on one side portion to join with a single cooperating strip located on the opposite side portion. A similar fastening arrangement can be employed to secure the thumb projection feature of said flexible substrate in place whereby one or more fastening strips extending therefrom can be joined to the same single strip being employed to fasten the releasable side strips thereto. The pliable nature of the flexible substrate along with the releasable fastening means being employed requires little effort by a wearer to secure it accurately in place while further enabling such device to be worn with maximum comfort and therapeutic benefit when the wearer performs customary work tasks. The elastic cuff provided at the palm end of the flexible substrate helps restrain physical movement of the applied device while further serving to block any entrance of dirt or other contamination during treatment. While many materials can be selected for suitable construction of the present flexible substrate to include natural and synthetic fabrics as well as comparable plastic materials, it is preferred that a selected material have sufficient porosity to provide some ventilation therethrough. Constructing an integral remedial device in the foregoing manner thereby affords relief to the wearer with minimum adjustment also being needed once such device has been secured firmly in place.

DETAILED DESCRIPTION OF THE PREFERRED EMBODIMENTS

Figure 1:
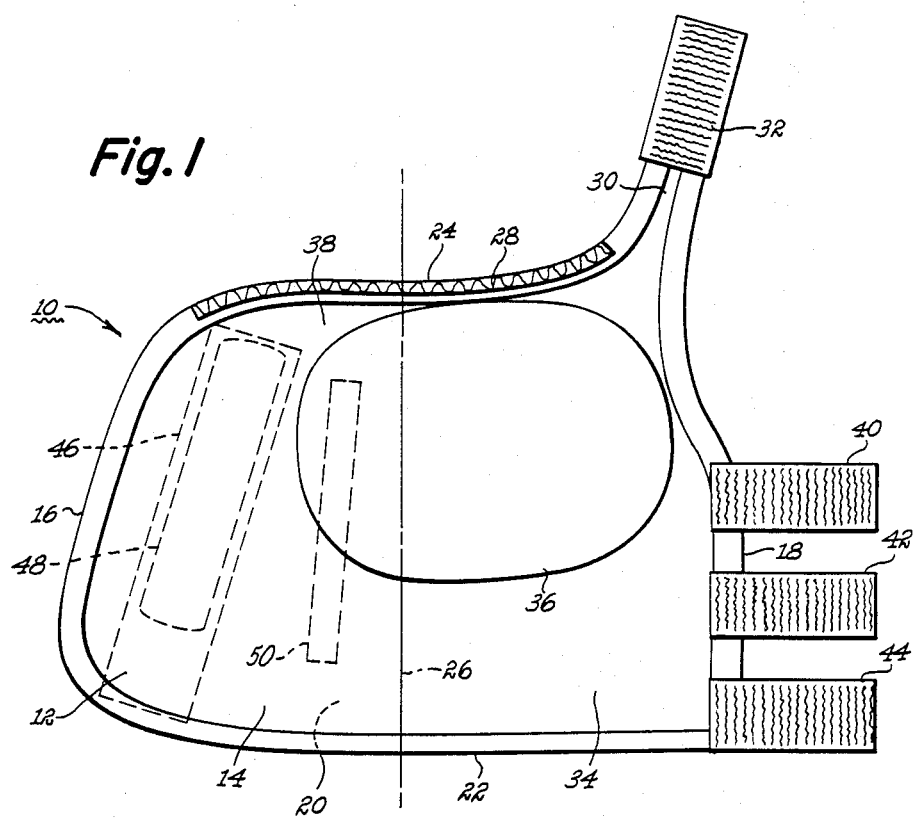
FIG. 1 is a plan view depicting the interior side if a typical remedial device according to the present invention before being applied to an ailing left wrist.
Figure 2:
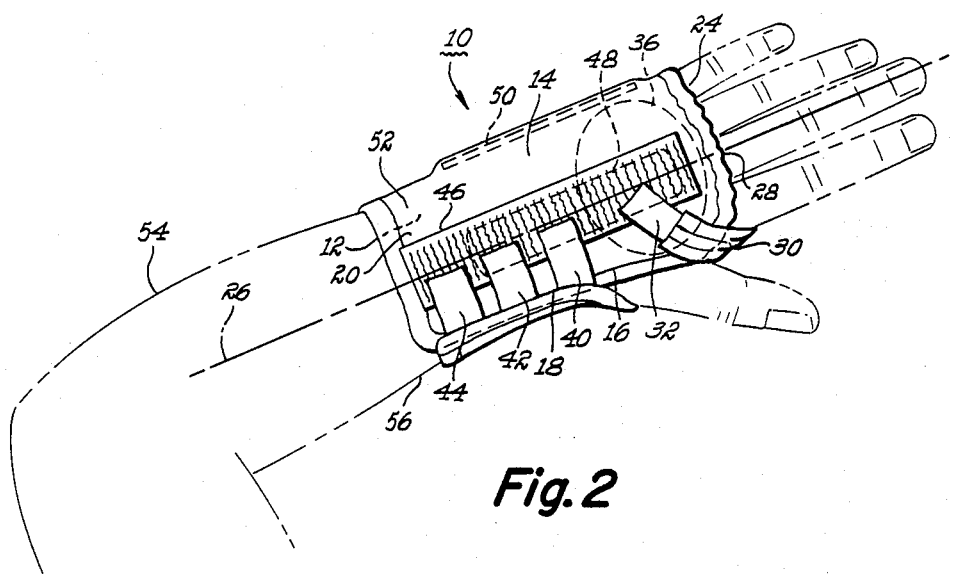
FIG. 2 is a plan view depicting the exterior side of the remedial device in FIG. 1 after having been secured to the ailing left wrist.

Referring to the FIG. 1, the depicted remedial device 10 is shown in a flat open position with its interior surface 12 facing upward. The device has a flexible substrate 14 of generally rectangular configuration with side portions 16 and 18 being readily visible. Top portion 20 of the flexible substrate in the depicted physical orientation rests intermediate the side portions 16 and 18, all of which can possibly better be perceived in FIG. 2. Lower end 22 of the flexible substrate 14 is intended to be secured to a person's left forearm with upper end 24 thereafter residing in the palm region of the person's left hand. When the flexible substrate 14 has been applied to an ailing left wrist in this manner its top or upper portion 20 can be seen to reside along the wearer's forearm longitudinal axis 26 as further depicted in FIG. 2. The palm or upper end 24 of the flexible substrate 14 further includes an elastic cuff portion 28 extending along its length together with a projection 30 extending forwardly therefrom. The projection 30 terminates with a releasable strip or tab 32 for the purpose of securing the palm end 24 of the flexible substrate 14 to the wearer. When secured in this manner, the projection 30 extends backwardly between the wearer's left thumb and forefinger as again shown in FIG. 2. Correspondingly, palm end 24 of the secured device can also be seen to terminate adjacent the metacarpal joints (not shown) of the wearer's hand. The flexible substrate 14 in the illustrated embodiment comprises a porous cloth material 34 to which is integrally joined still other essential features of the present device. A cushioning pad 36 is included in the palm region 38 of the flexible substrate 14 while releasable fastening means 40, 42 and 44 are joined thereto at side portion 18. Said releasable fastening strips engage a longitudinally extending releasable strip 46 disposed adjacent opposite side portion 16 of the flexible substrate 14 but which becomes aligned along its top or upper portion 20 when the device is applied to the wearer's wrist as shown in FIG. 2. Underlying strip 46 is a first splint member 48 which extends longitudinally along the wearer's point beyond the wrist. A second splint member 50 is integrally joined to the flexible substrate 14 adjacent to the first splint member but inward therefrom and which extends longitudinally in the same direction as the first splint member. When the device 10 is applied to the wearer's wrist said cooperating splint member 50 becomes aligned on the left side portion of said wrist as can be seen in FIG. 2. Accordingly, first splint member 48 primarily limits vertical movement of the wrist involved while splint member 50 cooperates in limiting lateral or horizontal wrist movement. Both splint members of a relatively rigid material such as metal or fiberglass can be sewn into enclosed pockets of the flexible substrate in a customary manner.

In FIG. 2 there is depicted a plan view of the FIG. 1 remedial device 10 which exposes its exterior surface 52. As shown, said device has been applied to an ailing left wrist of wearer 54 with the flexible substrate 14 fitting entirely around the wearer's forearm 56. Same numerals identify common features in said device 10 as previously employed in the FIG. 1 description. The applied device can be further seen to envelop the entire wrist region of a wearer extending beyond said wrist region in both longitudinal directions. Accordingly, the flexible substrate 14 is applied so that side portions 16 and 18 overlap with the releasable strip portions thereof 40, 42 and 44 being joined to a single releasable strip 46. Further engaging releasable strip 32 extending from projection 30 located at the palm end 24 of flexible substrate 14 to releasable strip 46 firmly secures device 10 in place. The cushioning pad 36 of flexible substrate 14 now rests against the left palm of the wearer while elastic cuff 28 effectively grips the wearer's hand around its entire periphery to avert contaminant entry. It also can be seen that first splint member 48 becomes positioned along the forearm longitudinal axis 26 when device 10 has been secured in place while cooperating second splint member 50 becomes aligned substantially coincident therewith on the left side of the wearer's wrist. A still further advantage achieved from constructing the flexible substrate of the illustrated device embodiment with cloth or plastic material is washability. Since this remedial device is customarily worn in a work environment over long periods, the relative ease with which such integral device can be readily washed represents a distinct improvement. It can further be appreciated that modifying the illustrated device to accommodate the same ailment in a right wrist of a wearer simply requires that the component parts of said embodiment be reversed so as to relocate the second splint member on the outside or right side of said wrist.

It will be apparent from the foregoing description that a remedial device has been provided which is particularly adapted for improved treatment of carpal tunnel syndrome. It is not intended to limit the present invention on the specific device embodiments herein illustrated, however, since persons skilled in the art will recognize that further modifications can be made therein without departing from the true spirit and scope of the present invention. For example, various materials can be employed in the construction of said device both for the flexible substrate portion as well as for splint members integrally joined thereto. Additionally, it is contemplated that still other known releasable fastening means can be employed in said device than herein illustrated with comparable results. A still further contemplated modification to the illustrated device utilizes integral cushioning means located under one or both splint members to provide added comfort for the wearer. Consequently, it is intended to limit the present invention only by the scope of the following appended claims:

What I claim as new and desire to secure by Letters Patent of the United States is:

1. A remedial device for treatment of carpal tunnel syndrome which permits limited wrist mobility by the wearer in both vertical and horizontal directions comprising in combination:
   (a) a flexible substrate sized to fit entirely around the wearer's forearm to form upper, lower and side portions when secured in place and which extends longitudinally at one end from a location below the wearer's elbow to an opposite palm end approaching the metacarpal joints of the wearer's hand, the palm end further terminating in an elastic cuff gripping the wearer's hand while also including a projection extending forwardly therefrom at the wearer's thumb before the device is secured in place but extending backwardly therefrom when secured in place,
   (b) a cushioning pad joined to the flexible substrate in the palm region,
   (c) a first longitudinally extending splint restraining excess vertical mobility of the wearer's wrist and joined to the flexible substrate in the upper portion,
   (d) a second longitudinally extending splint restraining excess horizontal mobility of the wearer's wrist and joined to the flexible substrate in a predetermined side portion, and
   (e) releasable fastening means joined to the flexible substrate enabling the side portions to be secured together while also enabling the hand projection to be secured to the top portion.

2. The device of claim 1 wherein permitted mobility is about the same in both vertical and horizontal directions.

3. The device of claim 1 wherein permitted mobility in at least one direction does not exceed about ten degrees with respect to the forearm longitudinal axis.

4. The device of claim 1 wherein permitted mobility in both directions does not exceed about ten degrees with respect to the forearm longitudinal axis.

5. The device of claim 1 wherein predetermined location of the second splint is fixed by the left or right wrist involved.

6. the device of claim 1 wherein both splints are formed with a relatively rigid material.

7. The device of claim 1 wherein the flexible substrate is formed with a cloth material.

8. The device of claim 7 wherein the cloth material is sufficiently porous to permit ventilation.

9. The device of claim 1 wherein the cushioning pad and splints permanently joined to the flexible substrate by fastening means.

10. The device of claim 1 having the splints permanently joined to the flexible substrate in enclosed pockets.

11. A remedial device for treatment of carpal tunnel syndrome in the left wrist of a person which permits limited wrist mobility by a wearer in both vertical and horizontal directions comprising in combination:
    (a) a flexible substrate sized to fit around the wearer's forearm to form upper, lower and side portions when secured in place and which extends longitudinally at one end from a location below the wearer's elbow to an opposite palm end approaching the metacarpal joints of the wearer's hand, the palm end further terminating in an elastic cuff gripping the wearer's hand while also including a projection extending forwardly therefrom at the wearer's thumb before the device is secured in place but extending backwardly therefrom when secured in place,
    (b) a cushioning pad joined to the flexible substrate in the palm region,
    (c) a first longitudinally extending splint restraining excess vertical mobility of the wearer's wrist and joined to the flexible support in the upper portion,
    (d) a second longitudinally extending splint joined to the left side portion of the flexible substrate, and
    (e) releasable fastening means joined to the flexible substrate enabling the side portions to be secured together while also enabling the hand projection to be secured to the top portion.

12. The device of claim 11 wherein permitted mobility is about the same in both vertical and horizontal directions.

13. The device of claim 11 wherein permitted mobility in at least one direction does not exceed about ten degrees with respect to the forearm longitudinal axis.

14. The device of claim 11 wherein permitted mobility in both directions does not exceed about ten degrees with respect to the forearm longitudinal axis.

15. A remedial device for treatment of carpal tunnel syndrome in the right wrist of a person which permits limited mobility by a wearer in both vertical and horizontal directions comprising in combination:
    (a) a flexible substrate sized to fit around the wearer's forearm to form upper, lower and side portions when secured in place and which extends longitudinally at one end from a location below the wearer's elbow to an opposite palm end approaching the metacarpal joints of the wearer's hand, the palm end further terminating in an elastic cuff gripping the wearer's hand while also including a projection extending forwardly therefrom at the wearer's thumb before the device is secured in place but extending backwardly therefrom when secured in place, (b) a cushioning pad joined to the flexible substrate in the palm region,
(c) a first longitudinally extending splint restraining excess vertical mobility of the wearer's wrist and joined to the flexible substrate in the upper portion.
(d) a second longitudinally extending splint joined to the right side portion of the flexible substrate, and
(e) releasable fastening means joined to the flexible substrate enabling the side portions to be secured together while also enabling the hand projection to be secured to the top portion.

16. The device of claim 15 wherein permitted mobility is about the same in both vertical and horizontal directions.

17. The device of claim 15 wherein permitted mobility in at least one direction does not exceed about ten degrees with respect to the forearm longitudinal axis.

18. The device of claim 15 wherein permitted mobility in both directions does not exceed about ten degrees with respect to the forearm longitudinal axis.

* * * * *